United States Patent [19]

Knapp

[11] Patent Number: 5,694,221
[45] Date of Patent: Dec. 2, 1997

[54] PARTICLE DETECTION METHOD FOR DETECTION OF CONTAMINATING PARTICLES IN SEALED CONTAINERS

[76] Inventor: Julius Z. Knapp, 22 Foxwood Dr., Somerset, N.J. 08873

[21] Appl. No.: 660,483

[22] Filed: Jun. 7, 1996

[51] Int. Cl.$^6$ ............................................. G01N 21/90
[52] U.S. Cl. .................................. 356/427; 250/223 B
[58] Field of Search ............................ 356/427, 426, 356/428, 237, 238, 240; 250/223 B

[56] References Cited

U.S. PATENT DOCUMENTS

| | | | |
|---|---|---|---|
| 3,627,423 | 12/1971 | Knapp et al. | 356/103 |
| 3,830,969 | 8/1974 | Hofstein | 178/6 |
| 3,914,058 | 10/1975 | Knapp et al. | 356/197 |
| 3,966,332 | 6/1976 | Knapp et al. | 356/197 |
| 4,209,802 | 6/1980 | Fogg et al. | 358/106 |
| 4,676,650 | 6/1987 | Bjorndal et al. | 356/427 |
| 5,365,343 | 11/1994 | Knapp | 356/427 |
| 5,523,560 | 6/1996 | Manique et al. | 250/223 |

*Primary Examiner*—Frank G. Font
*Assistant Examiner*—Michael P. Stafira
*Attorney, Agent, or Firm*—Graham & James LLP

[57] ABSTRACT

A method, and device for automated non-destructive deterministic inspection of solutions in transparent containers for particle contamination, comprising the steps of prepositioning particles in a zone distant from the vertical spin axis, specifically by tilting of the container; rapidly rotating the solution container; suddenly stopping the container, wherein particles within the solution, continue in motion; illuminating the container, while the particles are in motion, whereby particles within the container detectably reflect or block light. The container is tilted, prior to the spinning, by an acute angle ranging from 5° to 85°, from a normal concentric vertical spin axis of the container, whereby effects of gravity are utilized to affect settling of particles to provide improved uniformity of spin energy transfer to the contaminating particles within the container, wherein tilting of the container, results in gravity providing sectoral positioning of the contaminating particles to the lowest portion of the container. Settling of particles is estimated according to Stokes Law, prior to illumination inspection. Spinning of the container is either while the container is in the vertical or tilted position.

8 Claims, 3 Drawing Sheets

PARTICLE DETECTION METHOD FOR DETECTION OF CONTAMINATING PARTICLES IN SEALED CONTAINERS

FIELD OF THE INVENTION

This invention relates to procedures and devices utilized in the visual or optical inspection of transparent containers for the presence of contaminating particulate matter and particularly to inspection of injectable pharmaceutical preparations.

BACKGROUND OF THE INVENTION

There is a need to ensure that various transparent sealed containers are free of foreign contaminating particles. For food and beverage containers this is a market driven requirement. For containers of injectable pharmaceutical preparations, this is a legal requirement that must be satisfied, whenever possible, before the release of product for sale and use.

Transparent food and pharmaceutical containers are inspected for the presence of foreign particulates by various manual, semi-automatic and fully automatic inspection systems and devices. Two problems limit the accuracy that can be reached in the inspection for contaminating particles, both of which are ultimately based on economic restraints.

Since it is not economically feasible, under current technology, to inspect the entire fill volume of a container, only a proportion of the fill volume is actually inspected. The proportion of fill volume inspected imposes a probabilistic limit on the determination of particle contamination, being made with respect to of the full volume. Considerations of time and economics have worked to preclude inspection of the total fill volume, with certainty of particle contamination or not. Instead, a limited probabilistic decision must be made to arrive at the accept or reject determinations for the individual containers. The first limitation is therefore imposed by the percentage of the total fill volume of the container that is actually inspected, since the probability of rejecting particle contaminated containers cannot exceed the fill volume percent inspected in each container.

A common automated non-destructive inspection procedure for effecting such probabilistic determinations, is exemplified by U.S. Pat. Nos. 3,627,423 and 4,676,650. This procedure entails rapid spinning of the solution container, with the container being suddenly stopped. Because of inertia, particles within the solution, continue in motion, in generally decaying circular spirals. The orbits and decay times are related to the size, weight and hydrodynamic characteristics of the individual particles and to the viscosity of the suspending solution. The moving particles are then illuminated for inspection and the illuminated particle image signals are detected and evaluated for size and number. The particle movement and illumination thereof enables the ready differentiation of the moving particles from static imperfections in the container material, usually of a non-optical grade of glass and external container markings and debris.

A particularly useful refinement of this methodology, with which container volume can be more effectively inspected, is taught in U.S. Pat. No. 5,365,343, the disclosure of which is incorporated herein by reference thereto. In such methodology the containers are fully illuminated with forward scatter lighting with total light flux for detection of low contrast particles, with the size of the particles being evaluated by the maximum instantaneous increase of detector current as the particle moves through the detection zone. Simultaneously therewith, narrow detection volumes are back lighted with collimated light flux for detection of high contrast or dark particles, within the detection volume, by light extinction with a decrease of detector current from the normal non-particle illumination. The maximum pulsatile current decrease is used to determined the size of the particle.

However, despite improvements, and enhanced detection of both low contrast and high contrast particles, there still remains a second major limitation of the prior art methods of inspection. This limitation is attributable to the random position of the particles within the container at the start of each spin cycle and at the start of the inspection. As described, in order to distinguish between stationary optical marks on a container and particle contaminants in the liquid, particles in the liquid are put into motion, prior to the beginning of the inspection period with a spin and stop sequence around the vertical axis of the container. The path taken by the particles is essentially an orbital spiral around the vertical spin axis. Processing of the container image signals is then used to distinguish between the stationary defects and the moving contaminating particles. However particles within the container are randomly distributed at the start of the spin period and therefore their orbital velocities vary randomly, leading to inaccuracies in detection and measurement.

In the prior art, the spin cycle is selected to be a fraction of a second to achieve the desired high inspection rates. The transfer of velocity to particles within the container during the short spin cycle and the random particle position and orientation within the container combine to produce a random distribution of particle velocities and detectabilities during the inspection period. The random distribution of these particle velocities range from zero to some maximum value. For particles on or near the spin axis at the commencement of the spin cycle the transfer of particle velocity due to container spin is minimized. Those particle signals whose rotational velocity is less than the selected limit are processed as stationary defects and remain undetected. For platelet particulates, random orientation during detection injects an additional variable. The detected particle size varies from that of the edge to that of the desired flat surface.

The failure to detect the range of particles that have zero or near zero rotational velocity during the inspection period diminishes the effectiveness of the prior art contaminating particle inspections. When the movement of heavier fragments that rest on the bottom surface of the container are investigated it is seen that both their period of movement and their orbital velocity are reduced. Particles in this group are usually those found with high probability in cursory manual inspection at either the manufacturing site or preceding planned clinical usage.

The reason that these heavier, large particles are more difficult to detect is the reduction of spin energy transfer to them due to the friction encountered by the particle against the walls and bottom of the container during or immediately after the end of the spin cycle. Due to this friction, these heavier particles move with lower rotational velocity and stop moving well before the lighter liquid-borne particles. Secure detection of these heavier particles thus requires that the particle detection period commence as close as possible to the end of container spin period. Lighter particles, however, rotate at speeds close to the liquid rotational velocity in the outer volume zones of the container and detection thereof is as time limited. A false reject hazard results however from an inspection period which commences too close to the end of the spin period. This hazard is that the liquid meniscus breaks up into wavelets and cusps that reflect the inspection illumination onto the container walls producing signals indistinguishable from particle signals. The shortened particle movement time also sets an upper limit to a useful inspection period.

The initial position of the particle within the container is an important factor which should be taken into account in achieving more reliable inspections. In a typical container there are three general zones subject to particle inspection but which have separate character and inspection requirements in order to achieve greatest inspection accuracy. These zones include particles closest to the spin axis (hereinafter referred to as Zone A); particles closest to the container wall (Zone C); and particles in between Zones A and C (Zone B). Thus, with respect to the various zones:

ZONE A.

Following the spin and stop, and preceding the inspection for particles, fragments in Zone A will have low orbital speed if they remain in close proximity to the spin axis. Zone A particle fragments whose rotational center passes through the spin axis will have zero or near zero orbital speed.

ZONE B.

As a result of the use of the short spin times employed in order to achieve higher throughput rates, a fraction of the particles in Zone B achieve maximum orbital speed, the remainder achieve moderate to low orbital speeds.

ZONE C.

Particles in close proximity to the outer wall of the container usually achieve the desired high orbital speeds.

To optimize the signal to noise characteristic of practical particle detection systems, all prior systems are designed with a bandpass characteristic. The bandpass characteristic is adjusted to exclude extraneous signals with higher or lower frequency content than the desired particle signals. For optimum detectability of contaminating particles, the rotational velocity of all such particles should be adjusted to be approximately equal. When the particles are randomly distributed in the container prior to the start of the inspection period, the pass band of the detection system must be wide enough to accept at least the major portion of the particle signals if an effective inspection is to be achieved. This includes the portion of heavy particle signals that move more slowly due to an initial position at or near the spin axis of the container (Zone A). A consequence of this widened particle signal pass band is a reduction in the signal to noise characteristic of the particle detection system with a reduced particle size detection range.

At the present time there are no commercially available automated particle inspection systems that can achieve an acceptably secure match to manual inspection results, in a single inspection. Instead, a sequence of two inspections in which a container is rejected if a particle is detected in either inspection is employed. This inspection strategy, a "Reject in Two" inspection, is presently required to achieve inspection security results, equivalent to the benchmark manual inspection for visible contaminants. This is a game of chance technique to increase the effectiveness of the inspection, to match that of the required manual inspection, as required in system validation, prior to production use.

To make possible statistically replicable comparisons between the inspection results of a benchmark manual inspection and any proposed alternative method or device, container rejection probabilities, following earlier rule-of-thumb product quality categories have been separated into three statistically defined groupings:

1) An Accept Zone that includes containers from zero rejection probability to a maximum 0.30 rejection probability in a single inspection.

2) A Reject Zone is defined to include those containers with single inspection rejection probabilities from 0.70 to 1.00.

3) A Gray Zone: the Rejection probability region between 0.30 and 0.70 is the Gray quality Zone, The Accept Zone includes those usable containers with rejection probabilities from zero to 0.30. Particle contaminated containers that must be rejected are those identified in the manual inspection to be in the Reject Zone. These containers have single manual rejection probabilities equal to or greater than 0.70. The Gray Zone includes those containers with rejection probabilities greater than 0.30 and less than 0.70. This last group of containers is usable but will be sacrificed to maintain the security of inspection of those containers identified to be in the Reject Zone.

U.S. F.D.A. "Good Manufacturing Practices" requires a validation demonstration that any new system or device perform at least as effectively as the preceding system or device. This validation demonstration is accomplished by demonstrating that the inspected results of the automated system are equivalent to or better than manual inspection security results. This is performed by comparing the Reject Zone Efficiency achieved by both the manual and automated inspections. The Reject Zone Efficiency is calculated as the ratio of Reject Zone containers rejected in a single inspection to the total number of these containers that have been identified by the benchmark manual inspection procedure. This validation is a legally mandated prerequisite to any production use of such a system or device. Of equal importance is the economic effectiveness of an inspection. This is determined by the false reject rate of the inspection (the ratio of Accept and Gray Zone containers rejected in a single inspection) which is an excess cost of the inspection procedure.

In this "Reject in Two" type of inspection strategy, the ruling probability is that of accepting the Reject Zone containers that should be rejected. The net container rejection probability after the second inspection is calculated with Eq. 1. $P_R(2)$ is the rejection probability of a container after the second inspection. $P^2_A$ is the square of the probability of accepting a Reject Zone container in the first inspection.

$$P_R(2) = \sqrt{1 - P_A^2(1)} \qquad \text{Eq. 1}$$

The inspection results of the two different types of automated particle inspection systems, whose sales account for the major share of the market, can be analyzed with this equation. For particle detection systems using the sharpness of the particle image in their detection scheme, the detection volume is approximately 1 mm thick in a plane parallel to the imaging plane. For particle detection systems using a reduction in the light energy received to detect a contaminating particle, the sensing zone is a section 1 mm wide approximately perpendicular to the imaging plane. In each case, a particle that has just exited the detection zone, before the inspection period has begun, must traverse an orbit of approximately 180 degrees before re-entering the detection zone. The time required for a secure inspection is so long that it would result in uneconomic inspection rates. As a result, both of the automated inspection systems described use two short sequential inspection periods and reject a container if it is rejected in either of the two inspection periods. This decrease in detection capability of contaminating particles is greatest for the larger, heavier contaminating fragments that are securely detected by manual inspection procedures at both the manufacturing location and preceding planned clinical usage. In addition, the accept/reject decision process that results is imperfect. The containers rejected constitute a proportion of the Reject Zone containers and include a proportion of good, usable containers.

As described, in present and previous automated contaminating particle inspection art, the detection of contaminating particles within a container is preceded by a procedure to improve discrimination between optical container defects and external markings on the container walls and internal contaminating particles. In this procedure the contaminating particles are put into motion. Hardware or software processing of the container image is then used to distinguish between the stationary defects and the moving contaminating particles. However, none of the hardware or software improvements have provided deterministic accuracy.

It is an object of the present invention to provide a method in a particle detection system having enhanced reliability and minimized loss of inspection performance.

It is a further object of the present invention to economically utilize gravitational forces in providing the enhanced performance.

It is yet another object of the present invention to provide a method and device which converts standard probabilistic container inspections to an accurate and reliable deterministic inspection.

These and other objects, features and advantages of the present invention will become more apparent from the following discussion and the drawings in which:

SHORT DESCRIPTION OF THE DRAWINGS

SUMMARY OF THE INVENTION

Figure 1:
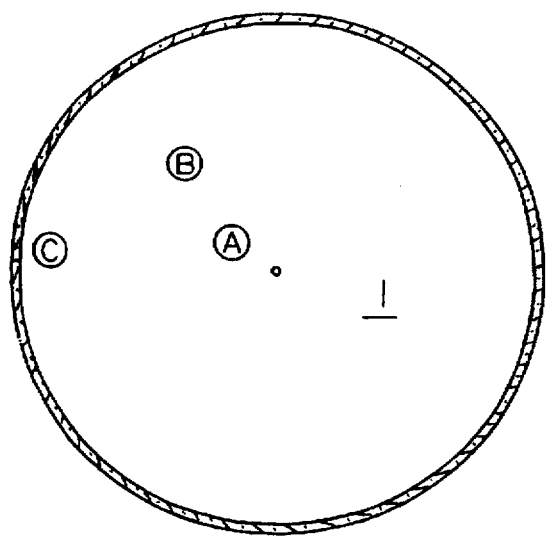
FIG. 1 is a cross sectional representational view of an ideal flat bottom of a container with a liquid volume having particle contaminants and the zone positions of the particles relative to the rotational or spin axis.

The present invention generally comprises a method, and a device used in the method, for automated non-destructive deterministic inspection of solutions and particularly injectable pharmaceutical solutions in transparent containers for particle contamination. The method comprises the steps of:

a) pre-positioning particles in a solution within the container into a predetermined volume zone, distant from a vertical spin axis;

b) rapidly spinning the solution container around its longitudinal axis;

c) suddenly stopping the container, wherein particles within the solution, continue in motion;

d) illuminating the container, while the particles are in motion, whereby particles within the container detectably reflect and/or block light.

In accordance with the preferred embodiment of the present invention, the improvement comprises tilting the container prior to the rotation or spinning (with appropriate physical support), by an acute angle ranging from 5° to 85°, from the normal concentric vertical spin axis, whereby the effects of gravity are utilized to affect settling of particles and particularly large particles into a lower quadrant of the container (heel portion). This serves to provide improved uniformity of spin energy transfer to the contaminating particles within the container when the container is spun thereafter. The combination of the prior art spin and stop particle movements, and the tilting of the container, results in gravity providing sectoral positioning of the contaminating particles within a sealed container. A spin cycle prior to the inspection spin cycle may be used to dislodge particle contaminants from the container walls. The result is two major inspection system improvements. The achievement of sectoral positioning results in 1) a more secure inspection for automated inspection systems (all of the particles thus positioned achieve an essentially uniform initial rotational velocity) and 2) a significantly shorter inspection period results (since the particles are positioned into an optimized fraction of the container volume prior to the spin & stop cycle, additional inspections are obviated). The decrease in the length of the secure inspection period serves to effectively increase and possibly double the rate at which containers are capable of being inspected for particle contamination compared to prior art methods.

The device of the present invention comprises the means for rotating, stopping and illuminating a transparent container having a liquid therein with possible particulate matter content, with means for capturing illumination information of particulate reflection and/or absorption. The device further comprises means for tilting the container at an acute angle from the vertical rotational axis whereby the force of gravity sectorally positions of the particles to a lower illuminated quadrant of the container.

DETAILED DESCRIPTION OF THE INVENTION

The method and device of the present invention, comprise modifications of existing methods and devices, (which use rotational positioning) to enable utilization of gravitational effects and time, to transform the inspection of injectable products from a probabilistic game of chance to a deterministic procedure by sectoral positioning of particles for complete or substantially complete inspection. This transformation improves Reject Zone container detection and reduces to near zero the false reject rate of good containers which injected an excess cost into the inspection but which was an acceptable additional expense in an era of expanding use of injectable antibiotic preparations with low container costs. Tighter control of inspection costs especially for the newer injectable products with much higher container value is now desirable and possible in accordance with the present invention.

To minimize the loss of inspection performance observed in prior art (with only a portion of particles being inspected), the contaminating particles present in the container are, in accordance with the present invention sectorally positioned in a selected illumination zone of the container using the force of gravity. Two practical methods to accomplish this end are possible with both using a container whose central axis is tilted from the vertical by an acute angle, prior to the spin & stop sequence, in a preferred range from 15 to 75 degrees. A 45° axial tilt, is a particularly preferred operating position. The spin time required to transfer adequate rotational energy to the particles for an effective inspection is reduced due to the more efficient coupling of spin energy to the liquid and hence to the contaminating particles made possible by the liquid volume centroid displacement from the spin axis. In both methods, the device utilized therewith embodies means for rotational tilting of the container during the inspection and prior to the spin and stop cycle.

The first method embodiment entails a degree of tilt great enough to overcome the static friction of the contaminating particle in moving to the lowest position in the container. This movement may be assisted by impulsive acceleration of the particle generated by movement of the container into the tilted position prior to entry into the spin & stop test position before the inspection commences.

An alternative second method embodiment is to introduce a short spin cycle with the container in either the upright or the tilted position, followed by a particle settling time period. The time required for this settling period is estimated using Stokes law settling time for a 100 µM borosilicate glass sphere. The choice of the 100 µM particle size is dictated by the fact that it is the threshold size for the 70% manual Reject Zone detection probability. With both the particle size and density determined, the 8.17 mm/sec. settling speed, the axial tilt of the container, the container diameter and the solution viscosity determine the settling time period required. According to Good Manufacturing Practices this initial estimate is then validated with a demonstration that the inspection security achieved with the automated inspection system is at least the equivalent of the preceding manual inspection.

The sectoral location of the heavy particles at the lowest portion of the container makes possible an effective reduction in the duration of the inspection cycle for either of the preceding particle sensing means employed. This reduction is achieved by arranging for the axial container tilt to occur in a plane parallel to the imaging axis. Placing the imaging axis parallel to a plane through the axis of the container and through its lowest position reduces the maximum orbital traverse required for particle detection from 180 degrees to 90 degrees for particle inspection systems using current art.

Spinning of the containers is either effected with the container remaining in the tilted position (with appropriate restraints during the spinning of the container along its longitudinal axis) or with the containers being brought into the vertical position after particle pre-positioning in the heel sector. The container is spun around its vertical axis with the particles having been pre-positioned in ZONE C. Means should be however be utilized to insure that particles in the pre-positioned zone are not moved from this zone by the return of the container to vertical positioning. In the vertical or upright position, the vertical spin axis coincides with the longitudinal axis of the container, whereas the vertical spin axis and longitudinal axis are separated, in the tilted position, by the angle of tilting.

DETAILED DESCRIPTION OF THE DRAWINGS AND THE PREFERRED EMBODIMENT

With specific reference to the drawings, FIG. 1 schematically depicts an ideal, flat, container bottom 1, with particle fragments in positions A, B and C, corresponding to Zones A, B and C, described above. The above discussion regarding the characterization of these positions is based on heavy fragments resting on an ideal flat surfaced bottom 1. Calculation of an angle of inclination for the bottom alone would normally provide a solution in providing the requisite tilt angle for rotation, to overcome the static friction of the particles or fragments encountered. However, actual production container bottoms can show tilt planes and can vary from those symmetrically convex around the axis of the container to eccentrically positioned concave and convex dimples in the container bottom. In any event, the disparities obtained from particles in the various positions is substantially lessened or even eliminated by the sectoral positioning of all the particles into an inspection sector.

Figure 2:
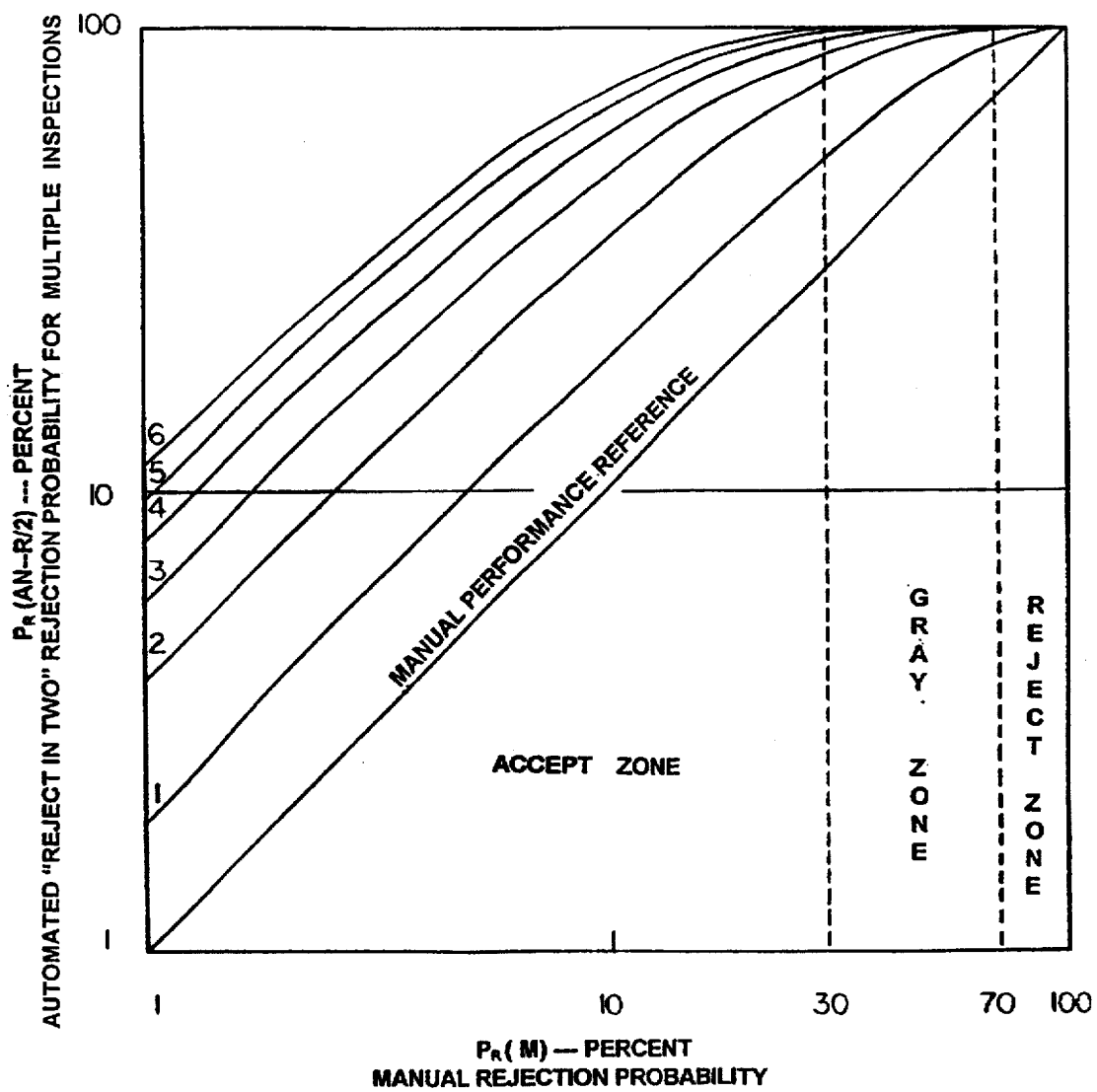
FIG. 2 is a graph showing the effect of the automated "Reject-in-Two" procedure of the prior art, relative to the rejection probability (inspection standard)

FIG. 2 presents a prior art graphical analysis of the effect of a "Reject in Two" automated particle inspection system as compared to the results of a standard manual inspection. Also shown in this Figure are the three particle contamination quality zones, Accept, Gray and Reject Zones, previously described. The area between the manual performance reference line and the curves for 1 to 6 repeated machine inspections visualizes the loss of good product whose quality matches that of the Accept and Gray Zones to achieve acceptably secure inspection performance in the Reject Zone. The increasing loss of good product with an increasing number of machine inspections shows the soft definition of the accept/reject decision in these inspection systems. An ideal inspection system would show zero rejects below the 70% rejection probability boundary and 100% container rejections above this boundary.

Figure 3:
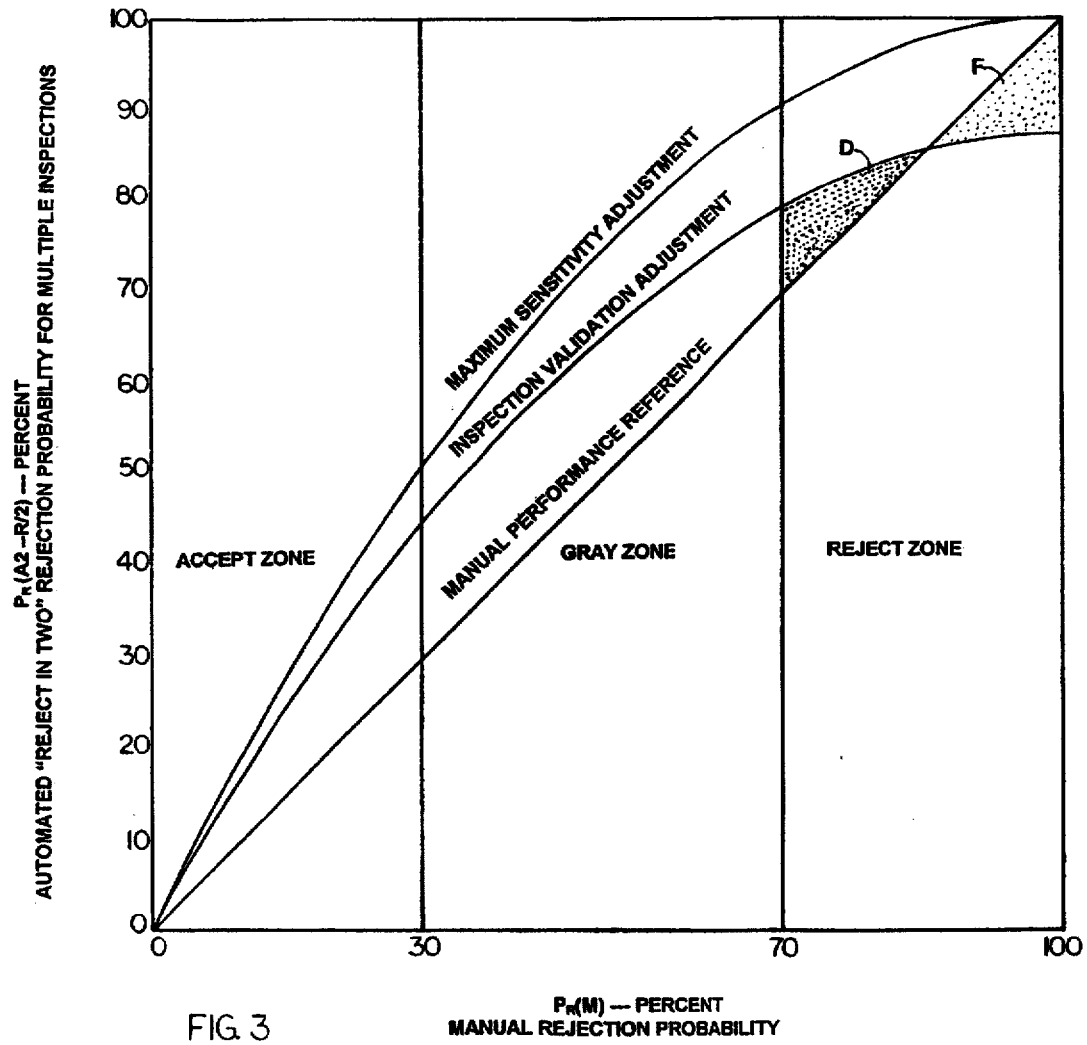
FIG. 3 is the graph of FIG. 2 with adjustments relative to a manual performance reference as used in the prior art.

With FIG. 3, the effect of adjusting the prior art inspection system to meet rather than to exceed the validation requirement can be seen. The economic cost of operating the inspection systems at maximum sensitivity in a single pass inspection is generally too high to be acceptable. The more usual operation mode of a "Reject in Two" inspection system is to operate in the validated adjustment mode shown in this Figure.

The probability of rejecting a container with a "visible" reject can be analyzed with a variety of life insurance statistics. The accept/reject decision for a single container in a single inspection cannot, except at a probability of zero or 1.00, be accurately predicted. The probability of an accept/reject decision for a group of containers, as the life expectancy for a group of people can be calculated with high accuracy. Application to the curves of FIG. 3 is based on a comparison of the area under the rejection probability curve in the Reject Zone for both methods, Validation of the automated system is achieved when the area under the automated rejection probability curve in the Reject Zone is equal to that of the area under the manual inspection probability curve in the reject zone. The adjustment shown in FIG. 3 is accomplished by selecting a sensitivity of inspection such that the area of the portion of the automated rejection probability curve in the Reject Zone in excess of the manual response probability curve, shown with heavier dots at D, is at least equal to the area of the Reject Zone Portion in which the response of the system is lower than that of manual inspection, shown in finer dots at F.

For any of the presently available particle inspection systems, the improved inspection resulting from particle pre-positioning provides a significant improvement in the quality of the inspection achieved. For an inspection system using the volume imaging technique taught in U.S. Pat. No. 5,365,343, the inspection of the total liquid volume in a container combined with particle pre-positioning results in a contaminating particle inspection that approaches a true deterministic inspection. The optimized distribution of particle velocities permits minimization of the pass band of frequencies required for analysis. This minimization results in an improved signal to noise limit for the particle inspection system thus extending the range of particle sizes that can be accurately determined. Additionally, the time required for a secure inspection is also reduced.

Figure 4:
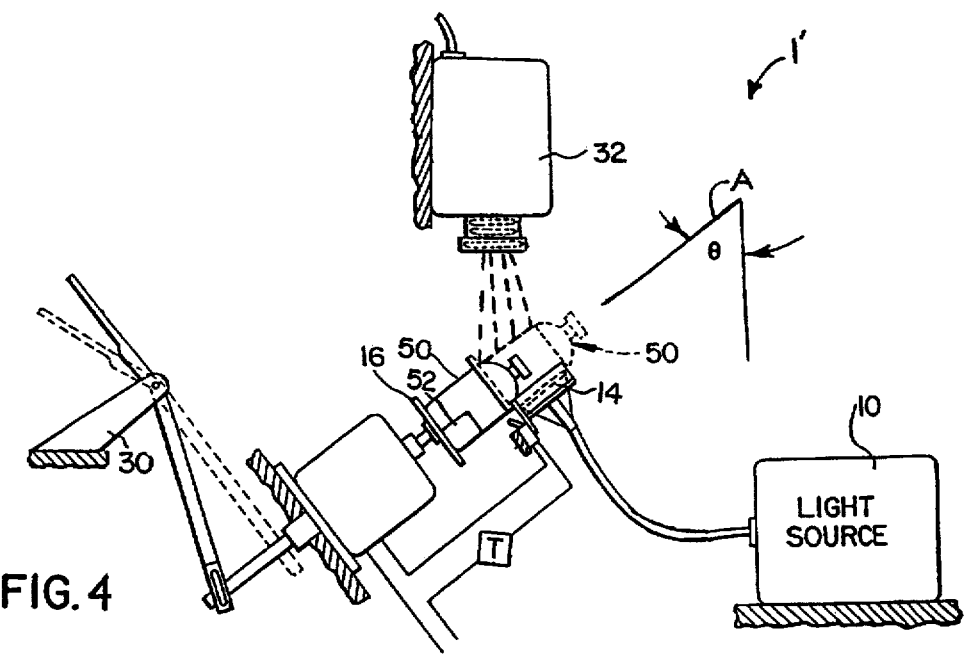
FIG. 4 depicts an apparatus arrangement for deterministic inspection in accordance with the present invention.

To assure positioning of the particle contaminants in the container in, at most, the heel of the lowest container quadrant, as shown in FIG. 4, an estimate of the settling time for the containers to reach that position in the maximum container size to be inspected is required. Using the results of the combination detection probability-holography study, a 50 µm particle is the minimum particle size to be considered a "visible" particle. Using a 32 mm outside diameter container with an inside diameter of 30 mm permits the use of Stokes law computations to estimate the settling time required for 50 μm glass particles to reach the desired heel position prior to the commencement of the spin and stop cycle. Table 1 tabulates Stokes law terminal settling speed for spheres in 20° C. still water in centimeters per second.

TABLE 1

STOKES LAW COMPUTATION OF TERMINAL SETTLING SPEED FOR SPHERES IN 20° C., STILL WATER, CM PER SECOND.

TERMINAL SETTLING SPEED, $-\frac{CM}{SEC}$

| PARTICLE DIAMETER μM | LATEX | GLASS | STAINLESS STEEL |
|---|---|---|---|
| 50 | 0.0072 | 0.218 | 0.950 |
| 100 | 0.029 | 0.817 | 3.800 |
| 200 | 0.115 | 3.482 | 15.200 |

Considering the longest path, in the largest small volume injectable container, to be 3.0 cm, settling time for the 50 μm sphere is approximately 15 seconds. Since the effect of frictional drag has been neglected, a 30 second period in the inclined position before the commencement of the spin cycle is employed.

To ensure that spot concavities and tilt planes do not bar particles from reaching the desired heel position prior to the spin and stop cycle, impact forces or vibration are used. The magnitude of the impact forces or vibration are adjusted below those at which cavitation bubbles will result.

In FIG. 4 the visual container inspection apparatus 1, as utilized in the present invention, is comprised of light source 10 and image capturing camera 32. A container 50 which is to be inspected for particulate matter is positioned on rotatable platform 16 which has an axis A which is offset from vertical position by acute angle θ (45° in the embodiment shown). Lever mechanism 30 permits movement of the platform along axis A to allow for positioning of the container 50 on the platform 16 and then into optical alignment with light emitting element 14 which is arranged parallel to vertical spin axis A. The container 50 is spun along axis A (clamping elements for holding the container in place during the spinning are standard and have not been shown, for purposes of clarity) with particles therein being located thereby in lower quadrant 52 and fully illuminated in about half the normal time required in prior art inspections. In addition, large particles normally located in Zone A are detected since they moved by the sectoral positioning into the lower detection quadrant.

It is understood that the above description and drawings are exemplary of the present invention and details contained therein are not to be considered as limitations on the present invention. Changes may be made to the structure and configuration of the inspection apparatus and to the inspection method without departing from the scope of the present invention as defined in the following claims.

What is claimed is:

1. A method, for automated non-destructive deterministic inspection of solutions in transparent containers for particle contamination, comprising the steps of:

a) pre-positioning particles in a solution within a vertically rotatable container having a vertical spin axis, with said particle being pre-positioned into a predetermined volume zone, distant from the vertical spin axis;

b) rapidly spinning a solution container around a longitudinal axis of the container;

c) suddenly stopping the container, wherein particles within the solution, continue in motion;

d) illuminating the container, while the particles are in motion, whereby particles within the container detectably reflect or block light; wherein the pre-positioning comprises tilting the container by an acute angle ranging from 5° to 85°, from a normal concentric vertical spin axis of the container, whereby effects of gravity are utilized to affect settling of particles to provide improved uniformity of spin energy transfer to the contaminating particles within the container, and wherein tilting of the container, results in gravity providing sectoral positioning of the contaminating particles to the lowest portion of the container; wherein the container is spun while in the tilted position.

2. The method of claim 1, wherein the angle of tilt is great enough to overcome any static friction of the particle in moving to the lowest portion of the container.

3. The method of claim 2, wherein the moving of the particles is assisted by impulsive acceleration of the particles generated by an additional step of movement of the tilted container into an inspection position.

4. The method of claim 2, wherein the acute angle of tilt ranges from 15° to 75°.

5. The method of claim 1, wherein the spin time is followed by a particle settling time period, with said settling time period being estimated using Stokes law settling time for a 100 μM borosilicate glass sphere with respect to the degree of the axial tilt of the container, the container diameter and the solution viscosity.

6. The method of claim 1, wherein the axial container tilt is arranged to occur in a plane parallel to an imaging axis, during detection of reflected or blocked light, with said imaging axis extending through the lowest portion of the container to reduce the maximum orbital traverse required for particle detection.

7. The method of claim 1, wherein the container is returned to a vertical position after the pre-positioning of the particles and prior to the spinning thereof, while maintaining the particles in the pre-positioned position.

8. A device for improved inspection of particulate matter containing in a solution within a transparent container in accordance with the method of claim 1, said device comprising:

a) means for pre-positioning particles in a solution within a container into a predetermined volume zone, distant from the vertical spin axis;

b) means for spinning the container along a longitudinal axis thereof stopping the spinning and illuminating the transparent container and possible particulate matter content;

c) means for capturing illumination information of particulate reflection and/or absorption; wherein the means for pre-positioning the container along a longitudinal axis thereof comprises means for tilting the container at an acute angle from a vertical rotational axis, prior to the spinning of the container, whereby the force of gravity helps sectorally position the particulate matter to a lower quadrant of the container; wherein the device further comprises means for spinning the container along its longitudinal axis while the container is in a tilted sectorally positioning position.

* * * * *